US005994502A

United States Patent [19]
Imperiali et al.

[11] Patent Number: 5,994,502
[45] Date of Patent: Nov. 30, 1999

[54] INHIBITORS OF OLIGOSACCHARYL TRANSFERASE

[76] Inventors: Barbara Imperiali, 2106 Lambert Dr., Pasadena, Calif. 91107; Jeffrey R. Spencer, 751 N. El Camino Real #101, San Mateo, Calif. 94401; Tamara L. Hendrickson, 276 S. El Molino Ave. #16, Pasadena, Calif. 91101

[21] Appl. No.: 08/914,494

[22] Filed: Aug. 19, 1997

Related U.S. Application Data

[63] Continuation of application No. 08/568,486, Dec. 7, 1995, Pat. No. 5,721,338.
[51] Int. Cl.$^6$ ............................. C07K 1/14; C07K 5/02; C07K 5/037
[52] U.S. Cl. ................... 530/344; 530/412; 530/317; 530/322
[58] Field of Search ................... 530/344, 322, 530/412

[56] References Cited

PUBLICATIONS

Tamara, G., ed., Table of Contents, *Tunicamycin*, (Japan Scientific Societies Press, 1986), pp. viii–xii.

Imperiali, Barbara and Karen L. Shannon, "Differences between Asn–Xaa–Thr–Containing Peptides: A Comparison of Solution Conformation and Substrate Behavior with Oligosaccharyltransferase," *Biochemistry*, vol. 30, No. 18, 1991, pp. 4374–4380.

Imperiali, Barbara et al., "Structural and Functional Characterization of a Constrained Asx–Turn Motif," *J. Am. Chem. Soc.*, vol. 116, No. 18, 1994, pp. 8424–8425.

Imperiali, B. et al., "A Mechanistic Proposal for Asparagine–Linked Glycosylation," *Reprinted from the Journal of the American Chemical Society*, 1992, 114.

Welply, Joseph K. et al., "Substrate Recognition by Oligosaccharyltransferase," *The Journal of Biological Chemistry*, vol. 258, No. 19, Oct. 10, 1983, pp. 11856–11863.

Ronin, Catherine et al., "Synthetic Substrates for Thyroid Oligosaccharide Transferase," *Eur. J. Biochem*, vol. 118, 1981, pp. 159–164.

Oda–Tamai, Sachie et al., "Decreased Transfer of Oligosaccharide from Oligosaccharide–Lipid to Protein Acceptors in Regenerating Rat Liver," *The Journal of Biological Chemistry*, vol. 260, No. 1, Jan. 10, 1985, pp. 57–63.

Behrens, Nicolás and Eduardo Tábora, "Dolichol Intermediates in the Glycosylation of Proteins." *Method in Enzymology*, 50:402–435, 1977.

Hubbard, S. Catherine and Raymond J. Ivatt, "Synthesis and Processing of Asparagine–Linked Oligosaccharides," *Ann. Rev. Biochem*, 50:555–83, 1981.

Ronin, Catherine et al., "Enzymatic N–Glycosylation of Synthetic Asn–X–Thr Containing Peptides," *FEBS Letters*, vol. 96, No. 1, Dec. 1978, pp. 179–182.

Sharma, Chandra B. et al., "N–Glycosylation of Yeast Proteins," *Eur. J. Biochem*, 116, pp. 101–108 (1981).

Chen, Winston W. and William J. Lennarz, "Metabolism of Lipid–linked N–Acetylglucosamine Intermediates," *The Journal of Biological Chemistry*, vol. 252, No. 10, May 25, 1977, pp. 3473–3479.

Hendrickson, T. L.; Imperiali, B. "Metal Ion Dependence of Oligosaccharyl Transferase: Implications for Catalysis," *Biochemistry* 1995, 34, 9444.

Imperiali, B.; Rickert, K. W. "Conformational implications of asparagine–linked glycosylation," *Proc. Natl. Acad. Sci. USA* 1995, 92, 97.

Imperiali, B.; Spencer, J. R.; and Struthers, M. D. "Structural and Functional Characterization of a Constrained Asx–Turn Motif," *J. Am. Chem. Soc.* 1994, 116, 8424.

Imperiali, B; Shannon, K. L.; and Rickert, K. W. "Role of Peptide Conformation in Asparagine–Linked Glycosylation," *J. Am Chem Soc.* 1992, 114,8642.

Hendrickson, T. L.; Sepncer, J. R. Kato, M. et al. "Design and Evaluation of Potent Inhibitors of Asparagine–Linked Protein Glycosylation," *J. Am Chem Soc.* 1996, 118, 7636.

*Primary Examiner*—Cecilia J. Tsang
*Assistant Examiner*—Michael Borin
*Attorney, Agent, or Firm*—Brinks Hofer Gilson & Lione

[57] ABSTRACT

The present invention provides novel inhibitors of oligosaccharyl transferase, methods for producing $Glc_3Man_9(GlcNAc)_2$—P—P—Dol, and methods for producing glycopeptides.

4 Claims, 3 Drawing Sheets

INHIBITORS OF OLIGOSACCHARYL TRANSFERASE

This application is a continuation of application Ser. No. 08/568,486 filed Dec. 7, 1995, now U.S. Pat. 5,721,338.

The U.S. Government has certain rights in this invention pursuant to Grant No. GM 39334 awarded by the National Institute of Health.

BACKGROUND OF THE INVENTION

1. Field of the Invention

The present invention provides inhibitors of oligosaccharyl transferase (OT), methods for obtaining $Glc_3Man_9$ $(GlcNAc)_2$-P-P-Dol, methods for obtaining glycopeptides and novel classes of antifungals,' antitumors and antivirals.

2. Discussion of the Background

The first committed step in the biosynthesis of all N-linked glycoproteins is catalyzed by the enzyme oligosaccharyl transferase and involves the transfer of a complex carbohydrate from a dolichol-linked pyrophosphate donor to the carboxamide side-chain of an asparagine residue (FIG. 1). Protein glycosylation is essential for the structure and function of many proteins and is involved in the control of many diverse biological processes (Paulson, Trends in Biol. Sci., 1989, 14, 272; Sadler, In Biology of Carbohydrates, 2nd Ed., Ginsburg & Robbins, Ed., John Wiley & Sons: New York, 1984, Vol. 2, pg. 87). For example, protein glycosylation has been found to be crucial for the development, growth and proper function of complex organisms, while, the aberrant glycosylation of proteins has been associated with diseased and transformed cells.

Despite the centrality of this biochemical transformation there are no synthetic or naturally occurring inhibitors that specifically target this enzyme-catalyzed reaction. In lieu of an inhibitor for OT, researchers have relied on the use of inhibitors of the dolichol phosphate cycle (FIG. 2).

For the synthesis of N-linked glycoproteins, the lipid linked oligosaccharide intermediate is $Glc_3Man_9(GlcNAc)_2$-P-P-Dolichol. This precursor unit is assembled by a series of reactions onto a lipid carrier, dolichol phosphate (reviewed by Parodi & Leoir, Biochem. Biophys. Acta, 1979, 550, 1–37; Sharon & Lis, In The Proteins, 3rd Ed., Neurath & Hill, Ed., Academic Press: London, 1975, Vol. 5, pg. 1). Dolichol serves to firmly anchor the carbohydrate close to the lumen side of the ER membrane near to the site of the emerging polypeptide.

The assembly of the oligosaccharide begins with the reversible transfer of N-acetylglucosamine 1-phosphate from UDP-GlcNAc to Dolichol-P (FIG. 2), followed by the irreversible transfer of N-acetylglucosamine, also from UDP-GlcNAc, to the GlcNAc-P-P-Dol to give $(GlcNAc)_2$-P-P-Dol. The β-linked mannose residues of the pentasaccharide core are transferred directly from GDP-Man to $(GlcNAc)_2$-P-P-Dol. Attachment of the remaining mannose residues, as well as of the three glucoses, is believed to proceed via the corresponding dolichol phosphate derivatives, formed respectively from GDP-Man and UDP-Glc. The ultimate product of this cycle is $Glc_3Man_9$ $(GlcNAc)_2$-P-P-Dol. The oligosaccharide is transferred en bloc from the lipid carrier to the nascent polypeptide. Thus, the final step of the dolichol cycle results in the transfer of a mannose-rich oligosaccharide chain to a polypeptide.

Tunicamycin, a glucosamine-containing antibiotic isolated from *Streptomyces lysosuperificus,* inhibits the first step in the dolichol phosphate cycle, the formation of GlcNAc-P-P-Dol (Tkacz & Lampen, Biochem. Biophys. Res. Commun., 1975, 65, 248). Other inhibitors include 2-deoxyglucose, 2-fluoroglucose, and 2-fluoromannose (Schwarz & Heath, Proc. Natl. Acad. Sci. USA, 1980, 77, 3811). These inhibitors compete for available dolichol phosphate and lead to formation of altered intermediates. However, these compounds are not recognized by OT and therefore inhibition of the overall reaction occurs only as dolichol phosphate supplies become exhausted.

Tunicamycin is described in U.S. Pat. Nos. 4,336,333 and 4,330,624. Unfortunately, tunicamycin is not specific for OT.

Further, tunicamycin is an extremely potent compound and must be used with extreme care. Thus, it is desirable to find inhibitors which are both specific for OT and whose toxicity can be controlled.

Inhibitors specific for OT would be useful both in pharmaceutical applications and in bioengineering applications.

Imperiali et al. (JACS, 1992, 114, 7942) describe a weak inhibitor (1 mM) of OT. The present application describes inhibitors of OT which are 10,000 times more potent than those previously described.

SUMMARY OF THE INVENTION

Accordingly, one object of this invention is to provide inhibitors of OT. Such inhibitors can be used in bioengineering applications to obtain quantities of $Glc_3Man_9$ $(GlcNAc)_2$-P-P-Dol, a metabolite currently available in limited quantities.

A second object of the present invention is to provide methods for obtaining $Glc_3Man_9(GlcNAc)_2$-P-P-Dol. This metabolite is useful as a substrate for N-glycoslating proteins and peptides.

A third object of the present invention is to provide a novel class of fungicidal agents.

Another object of the present invention is to provide a novel class of antitumor agents.

Another object of the present invention is to provide a novel class of antiviral agents.

These and other objects can be achieved by the present inventors' discovery of a new class of constrained peptides which are potent inhibitors of OT. This class is composed of cyclic peptides which contain 13 atoms in a ring which positions a hydroxy amino acid residue in proximity to an Axx residue as shown below in formula (I).

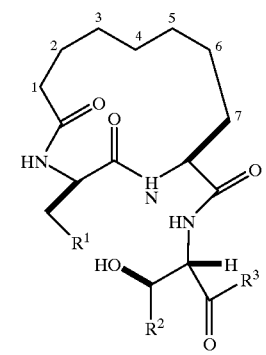

where each of the methylene units numbered 2–7 in the ring can be independently substituted with $CHR^6$, $CR^6_2$, NH, $NR^4$, O, S, S(O), or $S(O)_2$;

$R^1$ is $CH_2NH_3^+$ or $C(S)NH_2$;

$R^2$ is H or $C_{1-6}$ alkyl, preferably H or $CH_3$;

$R^3$ is an amino acid residue or a peptidyl chain, $OR^4$, $NHR^4$ or $NR^4_2$;

$R^4$ a substituted or unsubstituted $C_{1-20}$ alkyl, preferably $C_{1-6}$ alkyl; substituted or unsubstituted $C_{5-10}$ aryl, preferably phenyl; substituted or unsubstituted $C_{3-8}$ cycloalkyl; and $R^6$ is substituted or unsubstituted $C_{1-20}$ alkyl, preferably $C_{1-6}$ alkyl; substituted or unsubstituted $C_{5-10}$ aryl, preferably phenyl; substituted or unsubstituted $C_{3-8}$ cycloalkyl; hydroxyl; thiol or a halogen atom;

wherein suitable substituents are a halogen atom, hydroxyl, thiol, $C_{1-6}$alkyl, $C_{6-10}$aryl, $C_{3-8}$cycloalkyl, nitro or amino.

DETAILED DESCRIPTION OF THE PREFERRED EMBODIMENTS

Figure 1:
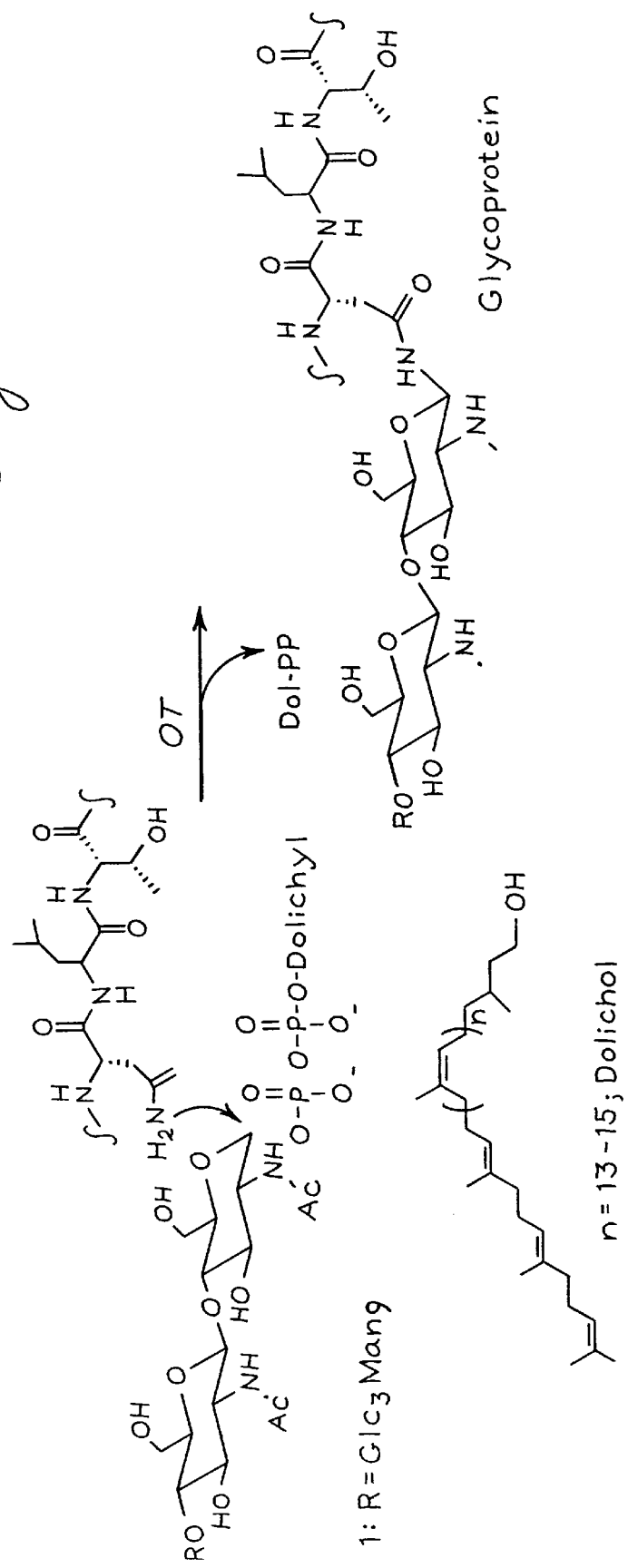
FIG. 1 is a schematic of the transformation catalyzed by OT.

The novel class of constrained ppeptidyl inhibitors of the present invention are represented by the following formula (I):

Compounds of the formula (I):

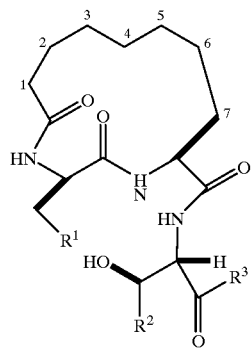

where each of the methylene units numbered 2–7 in the ring can be independently substituted with $CHR^6$, $CR^6_2$ NH, $NR^4$, O, S, S(O), or $S(O)_2$;

$R^1$ is $CH_2NH_{3+}$ or $C(S)NH_2$;

$R^2$ is H or $C_{1-6}$alkyl, preferably H or $CH_3$;

$R^3$ is an amino acid residue or a peptidyl chain, $OR^4$, $NHR^4$ or $NR^4_2$;

$R^4$ a substituted or unsubstituted $C_{1-20}$ alkyl, preferably $C_{1-6}$ alkyl; substituted or unsubstituted $C_{5-10}$ aryl, preferably phenyl; substituted or unsubstituted $C_{3-8}$ cycloalkyl; and $R^6$ is substituted or unsubstituted $C_{1-20}$alkyl, preferably $C_{1-6}$ alkyl; substituted or unsubstituted $C_{5-10}$ aryl, preferably phenyl; substituted or unsubstituted $C_{3-8}$ cycloalkyl; hydroxyl; thiol or a halogen atom;

wherein suitable substituents are a halogen atom, hydroxyl, thiol, $C_{1-6}$alkyl, $C_{6-10}$aryl, $C_{3-8}$cycloalkyl, nitro or amino.

Suitable halogen atoms include chlorine, fluorine, bromine or iodine.

Suitable amino acid residues include any synthetic or naturally occurring amino acid residue, which can be capped at the carboxyl terminus with an amine, hydrogen, a halogen atom, $C_{1-6}$ alkyl, $C_{6-10}$ aryl or $C_{1-6}$ alkyl $C_{6-10}$ aryl.

Suitable peptidyl chains comprise any number of amino acid residues, preferably 1–3 amino acid residues.

The essential features of this novel class of inhibitors are as follows:

a ring containing 13 atoms;

three consecutive peptide bonds; and a β-hydroxy amino acid residue and an Axx residue positioned in an Asx- or an Asx-like turn.

An Axx residue, as used herein, is an aminobutyrinyl amino acid (see Amb below) or a thioasparaginyl amino acid residue (see Tan below).

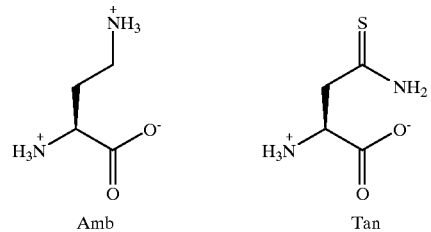

Amb                Tan

Asx-turns are defined by Baker & Hubbard (Prog. Biophys. Mol. Biology, 1984, 44, 97; incorporated herein by reference). An Asx-like turn, as used herein, contains the same backbone dihedral angles as in the Asx-turn, but lacks the hydrogen bond formed by the carboxyamide carbonyl of the asparaginyl residue.

The peptidyl inhibitors of the present invention can be synthesized using conventional techniques (see for example, M. Bodansky, Principles of Peptide Synthesis, Springer-Verlag: Berlin, 1984; Stewart & Young, Solid Phase Peptide Synthesis, Pierce: Rockford Ill., 1984; incorporated herein by reference).

1. Relocation of the thioether within the ring

The synthesis of the unnatural amino acid Aha is described below. A similar protocol can be used to generate analogs of Aha which vary in the length of the methylene chain. The cysteine and homocysteine analogs are commercially available, with the cysteine compound being used to generate the parent inhibitor. To afford cyclization, the capping reagent needs to be shortened by the same number of methylene groups as were added to the cysteine side chain. For example, when homocysteine is used in place of cysteine, bromopentanoic acid should be used as the capping agent. This will afford the same size cycle as in the parent inhibitor.

2. Introduction of an SO group within the ring

The sulfoxides can be directly generated from the parent thioethers described above. In each case, the thioether is dissolved in a solution of 5% hydrogen peroxide in water. Complete oxidation to the sulfoxide is typically afforded in 30–60 minutes. This process generates two diastereomeric sulfoxides which can be readily separated by HPLC (Barker, P. L. et al. J. Med. Chem. 1992, 35, 2040). The two diastereomers should exhibit different inhibitory properties.

3. Introduction of an $SO_2$ group within the ring

The sulfones can be generated by treating the parent thioethers with oxone (KHSO.) as described by Karl, R. M.; Hupperich, M.; Thomer, A.; Eggerer, H. Eur. J. Biochem., 1995, 227, 292. To avoid oxidation of the Amb sidechain under these conditions, it may be necessary to incorporate this residue into the peptide with an orthogonal protecting group such as an Alloc group. This protection would reduce the possibility of misoxidation on the Amb side chain.

4. Introduction of an NH group alone the ring

The synthesis of this compound can be obtained in a manner which is very similar to the parent thioether compound. During the initial peptide synthesis, the cysteine residue is replaced by an amino analog which is orthogonally protected with an alloc group. The completed peptide is capped with the appropriate alkylated halide. Four of the six amino acids which could be used are readily available (see Table 1). The remaining two amino acids (requiring bromoethanoic acid and bromoacetic acid as the capping reagents), are readily synthesizable from the analogous, unnatural carboxylate amino acid. Similarly to the-StBu group used in the synthesis of the thioether inhibitor, the alloc group can be cleaved from the peptide while leaving the remaining protecting groups intact. This deprotection can be accomplished, through standard protocols (for example see Albericio, F. et al. Peptides, 1993, 191), by treatment of the resin with Palladium tetrakis triphenylphosphine in the presence of acetic acid and a secondary or tertiary amine. Cyclization is then afforded by swelling the resin in DMF in the presence of a mild base as described for the parent thioether compound. The cyclization will most likely be substantially slower than that of the thioether compound as the primary amine is less nucleophilic than the thiolate. Substitution of the bromine with iodine may speed up the reaction time (possibly at the expense of purity).

TABLE 1

Introduction of an NH group into the inhibitor ring

| Amino Acid | Capping agent |
|---|---|
| Fmoc-Baa(Alloc) | Bromohexanoic acid |
| Fmoc-Amb(Alloc) | Bromopentanoic acid |
| Fmoc-Orn(Alloc) | Bromobutanoic acid |
| Fmoc-Lys(Alloc) | Bromopropanoic acid |

5. Introduction of a —CH$_2$— group along the ring

The preparation of the unnatural amino acid aminodecanedioic acid has already been described(Imperiali, B.; Spencer, J. R.; Struthers, M. D. J. Am. Chem. Soc., 1994, 116, 8424). This amino acid would need to be orthogonally protected before incorporation into the peptide (one possibility is an allyl ester protecting group). Cyclization can then be afforded on the resin by forming a side-chain to backbone amide bond through standard peptide synthesis procedures.

6. Introduction of a —O— or an —NR— group along the ring

These compounds are the most synthetically challenging of the different compounds. The easiest path would be to synthesize the unnatural amino acids analogous to Add (see section 5) but already including an ether linkage or the appropriate secondary amine. For example, to incorporate an oxygen in place of the sulfur in the gamma position (analagous to the replacement of cysteine with serine in the parent compound), the following unnatural amino acid could be used:

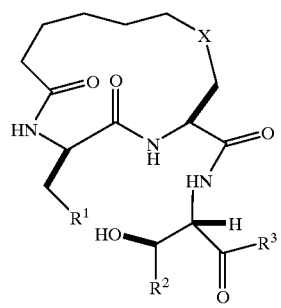

(II)

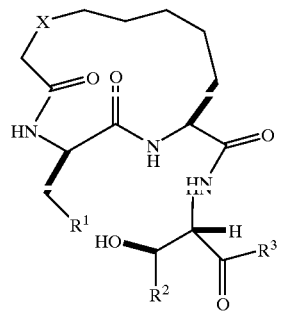

(III)

This amino acid would need to be appropriately protected for incorporation into the peptide prior to cyclization. Cyclization could then be afforded in the same manner as described in Section 5.

Preferred inhibitors of the present invention are of the formula (II) or (III):

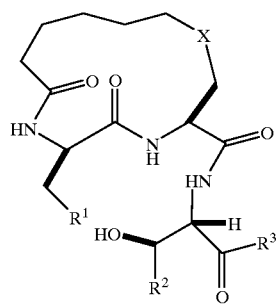

(II)

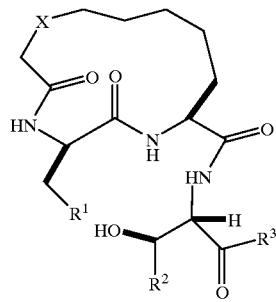

(III)

wherein X is NH, NR$^4$, O, S, S(O), or S(O)$_2$;

R$^1$ is CH$_2$NH$_{3+}$ or C(S)NH$_2$;

R$^2$ is H or C$_{1-6}$alkyl;

R$^3$ is an amino acid residue or a peptidyl chain, OR$^4$, NHR$^4$ or NR$^4{}_2$; and $R_4$ is a substituted or unsubstituted $C_{1-20}$ alkyl; substituted or unsubstituted $C_{5-10}$ aryl; substituted or unsubstituted $C_{3-8}$ cycloalkyl;

wherein suitable substituents are a halogen atom, hydroxyl, thiol, $C_{1-6}$alkyl, $C_{6-10}$aryl, $C_{3-8}$cycloalkyl, nitro or amino.

Inhibitors of the formula (I) can be obtained by substituting Tan for Asn in the synthesis described by Imperiali et al. (JACS, 1994, 116, 8424).

Figure 3:
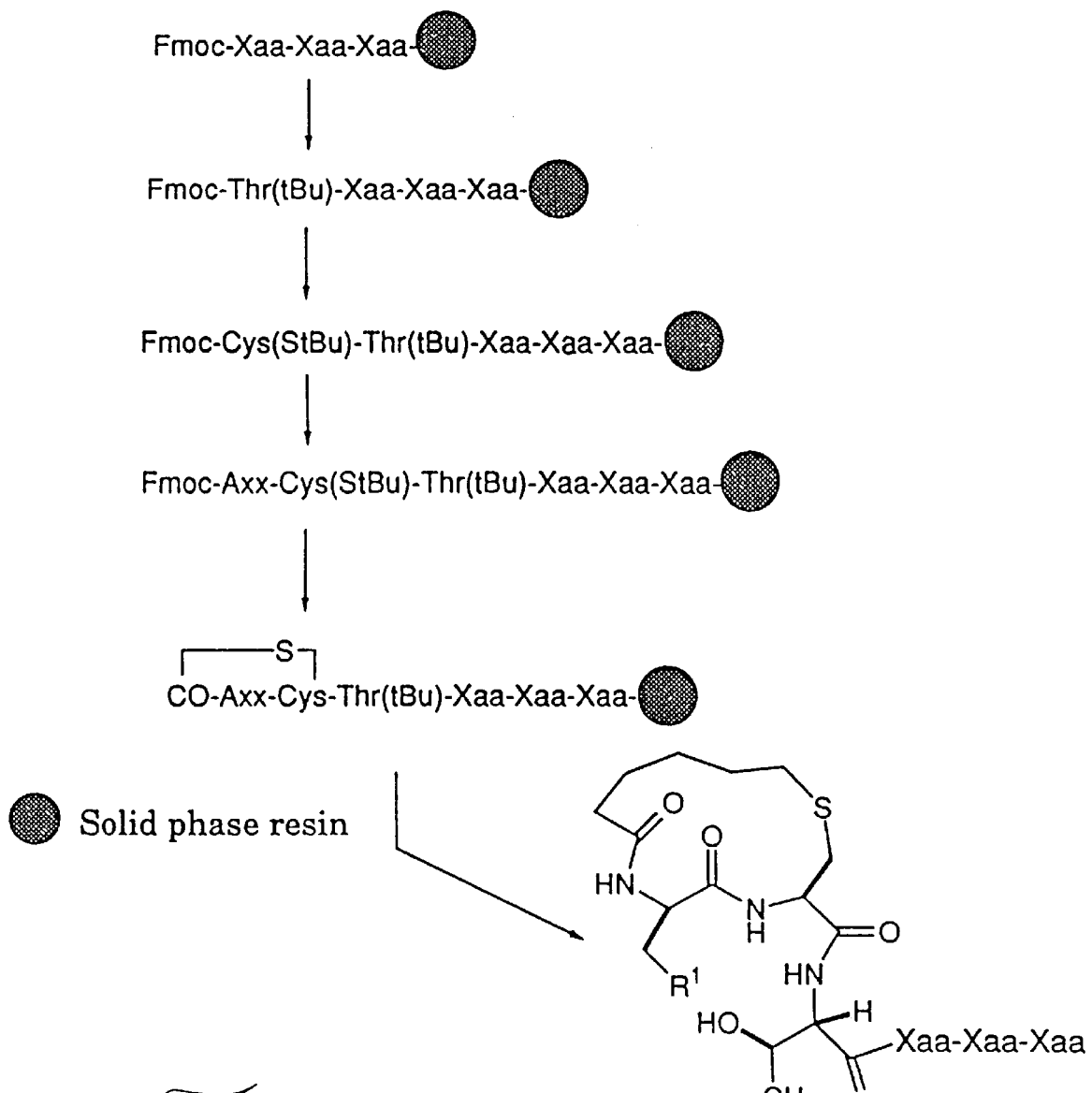
FIG. 3 is a schematic of the synthetic strategy used to obtain the OT inhibitors of the present invention.

In particular, inhibitors of the formula (II) or (III) can be obtained using solid phase peptide techniques as illustrated in FIG. 3 (shown for formula (II)) and described in detail in the examples below.

Figure 2:
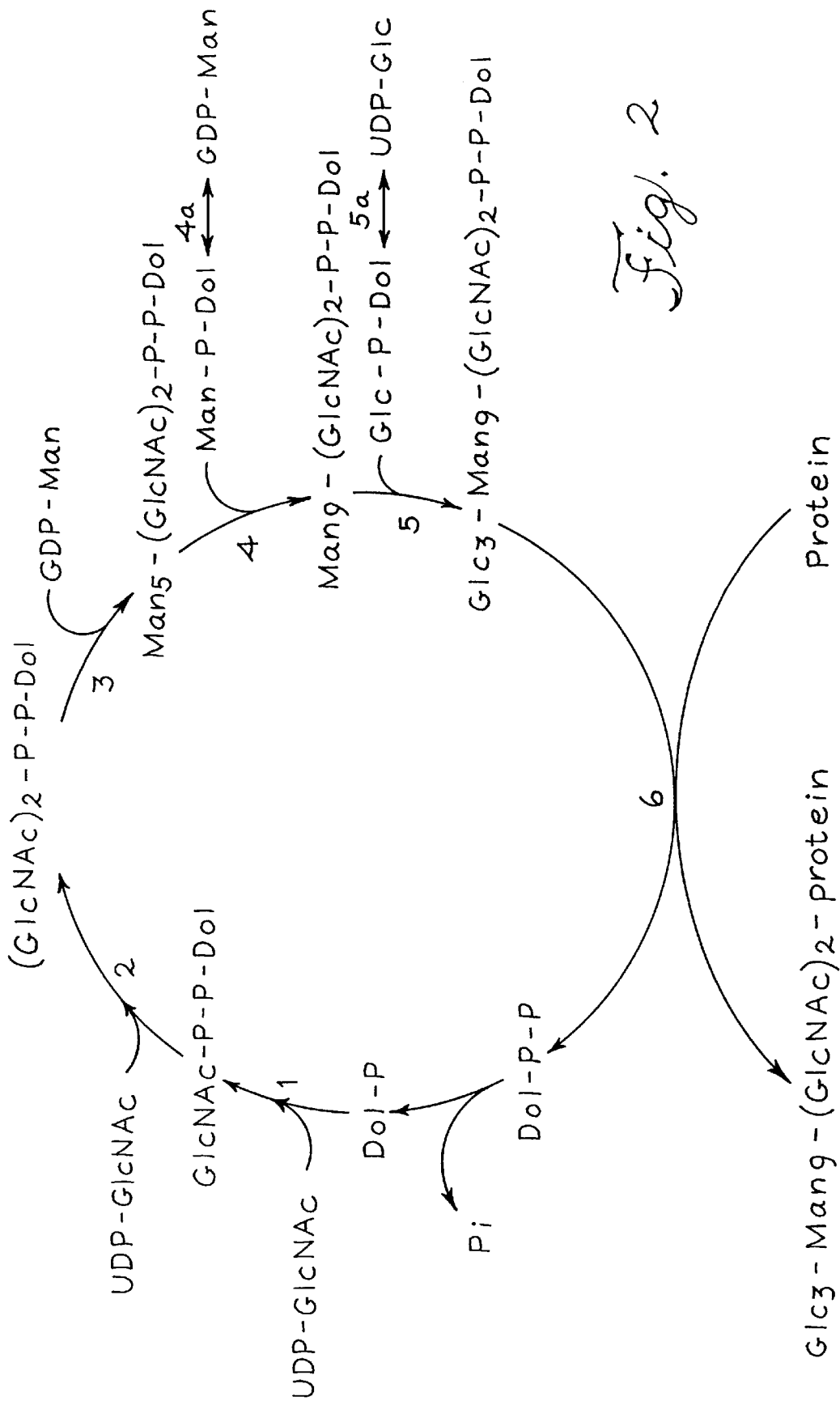
FIG. 2 is a schematic of the dolichol phosphate cycle.

The peptidyl inhibitors of the present invention can be used to obtain commercially useful amounts of $Glc_3Man_9$ $(GlcNAc)_2$-P-P-Dol. In a cell, OT catalyzes the transfer of the sugar, $Glc_3Man_9(GlcNAc)_2$, from the lipid donor, $Glc_3Man_9(GlcNAc)_2$-P-P-Dol, to a peptide, resulting in the biosynthesis of glycopeptides and glycoproteins. The inhibitors of the present invention can be used to prevent glycoprotein synthesis and thereby afford a pool of $Glc_3Man_9$ $(GlcNAc)_2$-P-P-Dol. Tunicamycin cannot be similarly used because it inhibits step 1 of the Dolichol phosphate cycle (FIG. 2) resulting in the depletion of the $Glc_3Man_9(GlcNAc)_2$-P-P-Dol pool.

$Glc_3Man_9(GlcNAc)_2$-P-P-Dol can be obtained from Dol-P and the appropriate nucleotide sugars (UDP-GlcNAc, GDP-Man and UDP-Glc). Dol-P is commercially available (for example from Sigma, St. Louis Mo.) or can be synthesized as described by Imperiali & Zimmerman (Tetrahedron Lett. 1988, 29, 5343). Dol-P, UDP-GlcNAc, GDP-Man and UDP-Glc are added to a microsomal extract in the presence of the peptidyl inhibitors of the present invention. A microsomal extract is described by Behrens & Tabora (Methods in Enzymol. 1977, 45, 402; incorporated herein by reference). The mixture is allowed to react for at least 1 hour and then quenched. $Glc_3Man_9(GlcNAc)_2$-P-P-Dol can be isolated and purified using known techniques such as extraction followed by ion exchange chromatography resin (see Behrens & Tabora, supra).

Alternatively, $Glc_3Man_9(GlcNAc)_2$-P-P-Dol can be obtained by contacting a whole cell with the inhibitors of the present invention. Here, endogenous pools of Dol-P and the various nucleotide sugars are used in the biosynthesis.

$Glc_3Man_9(GlcNAc)_2$-P-P-Dol can be used to synthesize glycoconjugates important in the field of pharmaceuticals and bioengineering applications under controlled conditions with OT.

A review article by Varki (Varki, A. Glycobiology, 1993, 3, 97) gives a thorough list of glycoproteins and their biological functions, particularly in regards to the role of the oligosaccharides. For example, glycoproteins can be used to obtain novel antibodies, vaccines, hormones, etc. Novel glycoproteins can be used as surfactants, lubricants, etc.Tables IX and XII in this paper, in particular, lists disease related roles of glycosylation and glycoproteins.

Additionally, glycosylation of peptides has been shown to increase the oral availability of certain inhibitors. For an example, see the paper on Somastatin (Albert, R.; Marbach, P.; Bauer, W.; Briner, U.; Fricker, G.; Bruns, C.; Pless, J. Life Sciences, 1993, 53, 517). Glycosylation has also been shown to increase the stability of peptides. For an example, see the paper on peptide stability in human serum (Powell, M. F.; Stewart, T.; Otvos, Jr., L.; Urge, L.; Gaeta, F.C.A.; Sette, A.; Arrjemois. T.; Thomson, D.; Soda, K.; Colon, S. M. Pharmaceutical Research, 1993, 10, 1268).

Glycoconjugates can be produced by modifying the procedure described by Imperiali & Rickert, PNAS USA, 1995, 92, 97–101. A mixture of $Glc_3Man_9(GlcNAc)_2$-P- P- Dol and a peptide containing a glycosylation site (Marshall, Ann. Rev. Biochem., 1972, 41, 673) is contacted with a microsomal mixture containing OT (see Behrens & Tabora, supra) for a time sufficient to allow transfer of the glycosyl moiety from dolichol to an appropriate Asn residue in the peptide. Formation of the glycopeptide or glycoprotein can be monitored by reverse phase HPLC (see Hendrickson & Imperiali, Biochemistry, 1995, 34, 9444).

In addition, D'Souza et al. (D'Souza, C.; Sharma, C. B.; Elbein, A. D. Analytical Biochemistry, 1992, 203, 211) have reported a method of preparing, isolating and purifying lipid-linked oligosaccharides at varying levels of oligosaccharide substitution. Two possibilities exist for the generation of. glycoproteins. OT may transfer shortened oligosaccharides to proteins. In this case, the methods described by D'Souza et al. could be readily used. For further modification of the lipid-linked oligosaccharide, or more probably, the glycoprotein, other glycosyltransferases and glycosidases would need to be used. Many of these enzymes have been overexpressed and characterized and could be used in much the same way as described for OT (see Schacter, H. In Molecular Biology, 1st ed, Fukuda & Hindsgaul, Ed., IRL Press, Oxford, 1994, pg. 88).

The peptidyl inhibitors of the present invention can also be used as antifungals, antivirals or antitumors. Suitable pharmaceutical compositions comprise (i) an inhibitor in accordance with the present invention and (ii) a pharmaceutical carrier.

The inhibitors of the present invention may be administered in the form of any conventional composition suitable for the mode of administration being used. Thus, in the case of topical administration, the inhibitor is preferably contained in an ointment, jelly, cream, lotion, etc. Such compositions may be either an oil-in-water or a water-in-oil emulsion. Alternatively, when the inhibitor is to be administered by injection, the inhibitor is suitably contained in a sterile solution or suspension. Suitable ingredients and procedures for forming suitable pharmaceutical compositions are disclosed in *Kirk-Othmer,* Encyclopedia of *Chemical Technology,* 3rd ed., Wiley, New York, Vol. 17, pp. 272–310 (1982), which is incorporated herein by reference. The pharmaceutical compositions of the present invention can be conventionally administered. For example, they can be administered topically, orally, parenterally, etc. Suitable dosages will vary depending on the age and size of the patient as well as the severity of the condition to be treated.

Having now fully described the invention, it will be apparent to one of ordinary skill in the art that many changes and modifications can be made thereto without departing from the spirit or scope of the invention as set forth herein.

EXAMPLES

1. Synthesis of the protected, non-natural amino acid Fmoc-Amb(Boc)-OH (1)

Fmoc-Amb(Boc)-OH (SIV.58). A heterogeneous mixture of Fmoc- Gln- OH (2.3 mmol, 0.85 g) and tert-butanol (15 mL) was placed in a dry flask, degassed under reduced pressure and placed under nitrogen. The mixture was warmed to 75° C. and lead tetraacetate (4.6 mmol, 2.05 g) was added. The dark orange mixture was allowed to stir at 75° C. for 1 h and was warmed to 80–85° C. for an additional 45 min, during which time the color lightened to pale brown. To the cooled (20° C.) mixture was added ether (50 mL) and $NaHCO_3$ (1 g). The suspension was allowed to stir for 20 min. The solids and salts were removed by filtration through a plug of silica gel followed by rinsing with $CHCl_3$/MeOH/AcOH:96/4/1. The foam obtained upon removal of the solvent was purified by silica gel chromatography (CHCl$_3$/MeOH/AcOH:96/4/1, R$_f$ 0.25). The product was obtained as a white powder (0.437 g, 43%) upon removal of solvent and crystallization in petroleum ether: mp 73.5–75.5° C., [α]$_D^{25}$+3.9° (c 1.0, CHCl$_3$), R$_f$ 0.36 (CHCl$_3$/MeOH/AcOH:95/5/1).

2. Synthesis of the linear hexapeptide Fmoc-Amb(Boc)-Cys (StBu)-Thr(OtBu)-Val(OtBu)-Thr(OtBu)-Nph-Resin Pal-Peg-PS resin (Millipore, 1.014 g, 0.170 meq/g) was loaded onto a Millipore 9050 column. The first four residues (Thr-Val-Thr-Nph) were coupled to the resin using standard Fmoc protected, free acid chemistry and enhanced monitoring. Fmoc-Nph (p-nitrophenylalanine) was purchased from Sigma and Fmoc-Cys(StBu),was purchased from NovaBiochem. All other amino acids were purchased, as the Fmoc derivatives, from Millipore. Coupling of the remaining two amino acids (Amb-Cys) was accomplished by hand on 20% of the resin (34 μmoles). The resin was washed with a 20% piperidine solution in DMF twice for three minutes each time, followed by two washes with DMF. A solution of Fmoc-Cys(StBu)-OH (48.8 mg, 113 μmoles, 3.3 eq), HOBT (19.1 mg, 125 μmoles, 3.7 eq), and DIPCDI (16.5 μl, 112 μmoles, 3.3 eq) was prepared in 2 mL DMF and added to the resin. Coupling was complete by Kaiser test after two hours. Resin was washed twice with DMF and then washed with Capping Solution (0.27 M HOBT, 0.3 M Acetic Anhydride, 20% DCM, 80% DMF) two times for two minutes each time, two washes with DMF and two washes with DCM. Fmoc-Amb(Boc) was coupled to the peptide using almost identical procedures (deprotection, coupling, capping) and a solution of Fmoc-Amb(Boc)-OH (46.8 mg, 106 μmoles, 3.1 eq), HOBT (16.7 mg, 109 μmoles, 3.2 eq) and DIPCDI (16.5 μL, 112 μmoles, 3.3 eq) in 2 mL DMF.

3. Synthesis of Bromohexanoyl- Amb(Boc)-Cys(StBu)-Thr (OtBu)-Val(OtBu)-Thr(OtBu)-Nph-Resin The Fmoc-Amb(Boc)-Cys(StBu)-Thr(OtBu)-Val(OtBu)-Thr(OtBu)-Nph modified resin was deprotected by washing twice with a 20% piperidine solution in DMF, followed by two washes with DMF and two washes with DCM. The resin was placed in a glass vial and combined with 3 mL DMF, 6-bromohexanoic acid (32 mg, 164 μmoles, 4.8 eq), DIPCDI (24 μL, 164 μmoles, 4.8 eq) and triethylamine (22 μl, 165 eq, 4.9 eq). This mixture was agitated for two hours and then the resin was filtered and resuspended in a solution of 6-bromohexanoic acid (33.6 mg, 164 μmoles, 4.8 eq) and DIPCDI (24 μL, 164 μmoles, 4.8 eq).

No additional triethylamine was added. This new mixture was agitated for 16 hours. Resin was filtered and washed two times with DMF and two times with DCM.

4. Synthesis of Cyclo(Amb(Boc)-Cys)-Thr(OtBu)-Val (OtBu)-Thr(OtBu)-NPh-Resin

The following deprotection and cyclization procedures were all performed in a glove bag under a nitrogen atmosphere (Virgilio, A. A. and Ellman, J. A. J. Am. Chem. Soc. 1994, 114, 11580). A solution of 5/3/2 n-Propanol/Dmf/water was prepared. Nitrogen was bubbled through this solution for 20 minutes. A solution of DMF was similarly treated. To remove the S-t-butyl protecting group from the cysteine residue, the Bromohexanoyl-Amb(Boc)-Cys (StBu)-Thr(OtBu)-Val(OtBu)-Thr(OtBu)-Nph modified resin was washed with 15 mL of the n-PrOH solution for ten minutes, filtered and recombined with an additional 15 mL of the n-PrOH solution and 375 μL tributylphosphine. This mixture was agitated occasionally over 6 hours. Following deprotection, the reaction was filtered and washed twice with methanol and twice with DCM. The resin was combined with 15 mL DMF for ten minutes, filtered and combined with 15 mL solution of DMF containing 375 μL 1,1,3,3-tetramethylguanidine (Aldrich). This mixture was protected from light and shaken for 20 hours. Following cyclization, the resin was filtered and washed twice with methanol and twice with DMF.

5. Synthesis and purification of Cyclo(Amb-CYs)-Thr-Val-Thr-Nph (2)

Cyclo(Amb(Boc)-Cys)-Thr(OtBu)-Val(OtBu)-Thr (OtBu)-Nph modified resin was treated with a 90/5/5 TFA/dimethyl sulfide/water solution for four hours to completely cleave the cyclized peptide. All remaining protecting groups were also removed during this treatment. The cleavage solution was triturated against diethyl ether twice to remove the cleavage reactants and produce the cyclic peptide as a solid, white powder. This powder was lyophilized from water overnight. Final purification was afforded by HPLC. A linear gradient of acetonitrile (0.1% TFA) and water (0.1% TFA) ranging from 35% ACN to 55% ACN over 20 minutes was employed. The cyclic peptide eluted at 8.4 minutes. The purified peptide was lyophilized to dryness to yield approximately 1 mg (1.2 μmoles).

6. Inhibition kinetics with 2 and S. Cerevisiae Oligosaccharyl Transferase

Compound 2 was assayed for competitive inhibition against a solubilized preparation of the yeast enzyme oligosaccharyl transferase. Three assays were performed: 1) a control with no inhibitor, 2) a 100 nM solution of 2 and 3) a 10 nM solution of 2. Prior to assaying, 26.3 μL of the crude enzyme were equilibrated for thirty minutes in the presence of 197.4 μL assay buffer (50 mM Hepes, pH 7.5, 1% Triton-X, 140 mM sucrose, 0.5 mg/mL phosphatidylcholine, and 10 MM MnCl$_2$) and 13.15 μL 750 μM Bz-Asn-Leu-Thr-NHMe in DMSO. The control also contained DMSO, while the 100 and 10 nM inhibitor solutions were prepared by the addition of 13.15 μL 2 μM and 0.2 μM DMSO solutions of 2, respectively. A 100,000 dpm aliquot of Dol-P-P-GlcNAc-[$^3$H]-GlcNAc (specific activity 36.5 Ci/mmol) was brought to dryness in an eppendorf. The lipid-linked donor was then redissolved 10 μL assay buffer. The assay was initiated by the addition of 190 μL of the equilibrated enzyme. Four time points were obtained by removing 40 μL aliquots at 1.5 minute intervals. Each aliquot was quenched in a solution of 1.2 mL 3/2/1 chloroform/methanol/4 mM MgCl$_2$. The aqueous layer was removed and the organic layer was washed twice with 0.6 mL TUP. The aqueous layers were combined and counted (dpm) in 5 mL Ecolite (ICN). The organic layers were brought to dryness under nitrogen. Solvable (200 μL, Dupont) was added to each organic fraction and agitated for 45 minutes. The organic layers were counted (dpm) in 7 mL Formula 989 (DuPont). Glycopeptide production is expressed as disintegrations per minute based on the values obtained from the dpms of the aqueous layer corrected for the total dpms in the aqueous and organic layers combined.

The control experiment had a rate of 701 dpm min$^{-1}$. The two experiments containing 2 exhibited slower rates of 296 and 572 dpm min$^{-1}$ for the 100 and 10 nM solutions respectively (see plot). The equation $K_i=([Inh]-i[Inh])/(i+([S]i/K_M))$ was used to determine a rough $K_i$ for 2. In this equation, [Inh] is the concentration of the competing inhibitor 2, [S] is the concentration of the competing substrate Bz-Asn-Leu-Thr-NHMe and [S]=37.5 μM, i is the percent inhibition of each experiment as compared to the control and $K_M$ is the binding constant of the competing substrate is equal to 25 μM. Using this equation, the 10 nM experiment yields a value for i of 0.184 and a $K_i$ of 18 nM, and the 100 nM experiment yields a value for i of 0.578 and a $K_i$ of 29 nM.

This equation is most accurate at values of i which approach 50% so the $K_i$ for 2 is approximately 29 nM.

7. Possible variations on the structure of 2

The cysteine residue and the capping agent used for the final cyclization can be replaced to yield similar compounds wherein the sulfur is displaced by any number (between 1 and 5) of methylenes within the cycle. For example, one possible structure (3) can be derived from the bromoacetylated peptide BrAc-Amb-Aha-Thr-Val-Thr-Nph, wherein Aha represents the unnatural residue 2-amino-7-thiohexanoic acid, incorporated into the peptide as Fmoc-Aha(StBu)-OH (4) and cyclized in the same manner as 2, only with a bromoacetyl cap rather than the bromohexanoic cap previously used.

Additionally, oxidation of the thioether bond in 2, or other analogous structures, can be afforded by dissolving the peptide in a 5% hydrogen peroxide solution in water and stirring for 30 minutes. The reaction is quenched by the addition of an equal volume of 0.1 % TFA in acetonitrile. The two diastereomeric sulfoxides (5a, 5b, shown derived from 2) that are produced can be separated by HPLC and assayed as described above.

8. Synthesis of Fmoc-Aha(StBu)-OH (4) for incorporation into 3

(S)-2-(97-luorenylmethoxycarbonyl)amino-7-chloroheptanoic acid (−)-pseudoephedrinyl amide (SIV.57). The amine, (S)-2-amino-7-chloroheptanoic acid (−)-pseudoephedrinyl amide (1.8 mmol, 0.59 g) (for reference, Myers, A. G. et al. J. Am Chem Soc. 1995, 117 8488), was dissolved in 7.2 mL of a heterogeneous mixture (1:1 v/v) of dioxane and saturated aqueous $NaHCO_3$. The mixture was degassed under reduced pressure, placed under nitrogen and chilled to 0° C. To the mixture was added Fmoc-OSu (2.2 mmol, 0.73 g) in four equivalent portions over 15 min. Another 1 mL of dioxane was added to improve solubility of the Fmoc-OSu. The mixture was allowed to stir 20 min at 0° C. and 4 h at 20° C. After the mixture was concentrated under reduced pressure, it was extracted into AcOEt (250 mL). The organic layer was washed with saturated aqueous $NaHCO_3$ (3×5 mL), saturated NaCl (3×5 mL) and dried ($MgSO_4$). After the solvent was removed under reduced pressure, the residue obtained was purified by silica gel chromatography (AcOEt/hexanes:40/60%). The protected compound was obtained as a white foam (0.823 g, 83%) after removal of solvents under reduced pressure: $[\alpha]_D^{25}$− 503.70° (c 0.01, $CHCl_3$), $R_f$ 0.25 (AcOEt/hexanes:1/1).

(S)-2-(9-Fluorenylmethoxycarbonyl)amino-7-chloroheptanoic acid (SIV.59). A suspension of (S)-2-(9-fluorenylmethoxycarbonyl) amino-7-chloroheptanoic acid (−)-pseudoephedrinyl amide (1.6 mmol, 0.823 g) in dioxane (12 mL) and 9 N $H_2SO_4$ (12 mL) was degassed under reduced pressure and placed under nitrogen. The mixture was heated to reflux for 6.5 h. After the mixture was cooled back to 20° C., it was concentrated under reduced pressure and extracted with AcOEt (3×75 mL). The pooled organic layers were washed with saturated NaCl (3×5 mL) and dried ($MgSO_4$). The residue obtained following removal of the solvent under reduced pressure was fractionated by silica gel chromatography ($CHCl_3$/MeOH/AcOH:95/5/1). The Fmoc protected amino acid was isolated as a pale amber solid (0.503 g) after removal of solvent and crystallization in hexanes. A more polar fraction was also obtained which, when subjected to 3 h more of hydrolysis in 1:1 dioxane/9 N $H_2SO_4$ (4 mL) and similar purification, afforded an additional 0.050 g of Fmoc protected amino acid (net 0.553 g, 86%): mp 114.0–116.0° C., $[\alpha]_D^{25}$+11.3° (c 1.4, $CHCl_3$), $R_f$ 0.39 ($CHCl_3$/MeOH/AcOH:95/5/3).

(S)-2-(9-Fluorenylmethoxycarbonyl)amino-7-iodoheptanoic acid (SIV.61). A saturated solution of sodium iodide in acetone was prepared from dry sodium iodide (stored over $P_2O_5$ under reduced pressure) and dry acetone (stored over $MgSO_4$ several days). A mixture of the chloride, (S)-2-(9-fluorenylmethoxycarbonyl) amino-7-chloroheptanoic acid (1.1 mmol, 0.553 g), and 15 mL of the saturated NaI/acetone solution was placed in a dry flask, degassed under reduced pressure, and placed under nitrogen. The mixture was heated at reflux (approximately 65° C.) for 5 h at which time the progress was checked by $^1$H-NMR spectroscopy. It was observed that approximately 15% of the chloride remained and the reaction was allowed to proceed at reflux for another 3 h until no chloride remained. The solvent was removed under reduced pressure and the residue obtained was suspended in AcoEt (200 mL). The organic layer was washed with $H_2O$ (3×5 mL) and dried ($MgSO_4$). The iodide was obtained as an amber solid (0.668 g, 98%) after removal of solvent under reduced pressure and crystallization in hexanes: mp 127.0–129.0° C., $[\alpha]_D^{25}$+14.1° (c 1.1, $CHCl_3$), $R_f$ 0.39 ($CHCl_3$/MeOH/AcOH: 95/5/3).

(S)-2-(9-Fluorenylmethoxycarbonyl)amino-7-(S-tert-butyldithio)-heptanoic acid (SIV.65). A mixture of sodium hydride 60 % dispersion (0.73 mmol, 0.029 g) and anhydrous THF (1.2 mL) in a dry flask was chilled (° C.) under nitrogen. The mixture was treated with tert-butyl mercaptan (0.73 mmol, 0.082 mL). After 15 min the heterogeneous mixture was allowed to warm to 20° C. for 20 min and then was chilled again to 0° C. In a separate flask, a solution of (S)-2-(9-fluorenylmethoxycarbonyl)amino-7-methanetiolsulonatoheptanoic acid (0.60 mmol, 0.285 g) in THF (1.2 mL) was chilled (0° C.) and transferred via cannula into the flask containing the tert-butyl thiolate mixture. Additional THF (0.4 mL). was used to rinse. The reaction was allowed to proceed 30 min at 0° C. and then to warm to 20° C. After 4h the mixture was chilled to 0° C. again and an additional portion of tert-butyl thiolate was introduced via cannula. The thiolate was prepared by a similar procedure from NaH (0.15 mmol, 0.006 g), THF (0.25 mL) and tert-butyl mercaptan (0.15 mmol, 0.017 mL) and added at 0° C. The reaction mixture was allowed to proceed 10 min at 0° C. and 1 h at 20° C. The mixture was once again chilled to 0° C. and treated with saturated aqueous sodium bicarbonate (1.5 mL) and FmocOSu (0.30 mmol, 0.10 g). After 20 min at 0° C. and 2 h at 20° C., the mixture was concentrated under reduced pressure. The aqueous layer was washed with petroleum ether (2×10 mL), chilled (0° C.), acidified with 1 M HCl and extracted with AcOEt (3×75 mL). The organic layer was washed with 0.1 M HCl (5 mL) and saturated NaCl (3×10 mL) and dried ($MgSO_4$). Upon removal of solvent, a pale yellow residue was obtained which was purified by silica gel chromatography (MeOH/$CHCl_{3:0 / 10}$%). The solvents were removed under reduced pressure, and the product was obtained as a white solid after crystallization in petroleum ether (0.218 g, 75%): mp 85.0–87.0° C. dec., $[\alpha]_D^{25}$+16.00 (c 0.45, $CHCl_3$), Rf 0.37 (AcOEt/MeOH.: 9/1).

List of Abbreviations

Ac, acetyl; ACN, acetonitrile; AcOEt, ethyl acetate; AcOH, acetic acid; Amb, γ-aminobutyrine; Tan, thioasparagine; Boc, t-butoxycarbonyl; Bz, benzoyl; $CHCl_3$, chloroform; CI HRMS, chemical ionization high resolution mass spectroscopy; DCM, dichloromethane; DIPCDI, diisopropylcarbodiimide; dpm, disintegrations per minute; DMSO, dimethyl sulfoxide; DMF, dimethylformamide; Dol, dolichol; Dol-P, dolichol phosphate; Dol-PP, dolichol pyrophosphate; Fmoc, fluorenylmethoxycarbonyl; Glc, glucose; GlcNAc, N-acetylglucosamine; Hepes, N-(2-hydroxyethyl)-piperazine-N'-(2-ethanesulfonic acid); HOBT, hydroxybenzotriazole; HPLC, high performance liquid chromatography; Man, mannose; MeOH, methanol; MHz, Nph, nitrophenylalanine; NP-40, Nonidet P-40; NMR, nuclear magnetic resonance; OSu, hydroxysuccinimide; OT, oligosaccharyl transferase; PC, phosphatidylcholine; TFA, trifluoroacetic acid; TLC, thin layer chromatography; TUP, theoretical upper phase; UDP- GalNAc, uridine diphosphate-N-acetylgalactosamine; All naturally occurring amino acids are referred to by their standard three-letter code.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A process comprising for isolating an asparaginyl-linked glycopeptide comprising:

contacting (i) a peptide containing an asparaginyl residue in a glycosylation recognition motif,
   (iia) a cell or cell fraction containing greater than endogenous amounts of $Glc_3Man_9(GlcNAc)_2$-P-P-Dol or (iib) substantially pure $Glc_3Man_9(GlcNAc)_2$-P-P-Dol, and
   (iii) oligosaccharyl transferase; and isolating a glycopeptide with a $Glc_3Man_9(GlcNAc)_2$- group attached to said asparaginyl residue.

2. The process of claim 1, wherein a cell containing greater than endogenous amounts of $Glc_3Man_9(GlcNAc)_2$-P-P-Dol is used.

3. The process of claim 27, wherein a cell fraction containing greater than endogenous amounts of $Glc_3Man_9(GlcNAc)_2$-P-P-Dol is used.

4. The process of claim 19, wherein substantially pure $Glc_3Man_9(GlcNAc)_2$-P-P-Dol is used.

* * * * *

UNITED STATES PATENT AND TRADEMARK OFFICE
CERTIFICATE OF CORRECTION

PATENT NO. : 5,994,502  
DATED : November 30, 1999  
INVENTOR(S) : Imperiali et al.

Page 1 of 1

It is certified that error appears in the above-identified patent and that said Letters Patent is hereby corrected as shown below:

On the Title Page

Column 1:
Line 1, under "PUBLICATIONS" delete "Tunicamycin, (Japan" and substitute --Tunicamycin (Japan-- in its place.

Column 2:
Line 11, delete "N-Glycosylation" and substitute --*N*-Glycosylation-- in its place.
Line 14, delete "N-Glycosylation" and substitute --*N*-Glycosylation-- in its place.
Line 17, delete "N-Acetylglucosamine" and substitute --*N*-Acetylglucosamine-- in its place.
Line 31, delete "114,8642." and substitute --114, 8642.-- in its place.
Line 32, delete "Sepncer, J.R." and substitute --Spencer, J.R.-- in its place.

Signed and Sealed this

Nineteenth Day of June, 2001

*Attest:*

*Attesting Officer*

NICHOLAS P. GODICI
*Acting Director of the United States Patent and Trademark Office*